United States Patent [19]

Sung

[11] 4,311,526

[45] Jan. 19, 1982

[54] γ2 - FREE, LOW COST AMALGAM ALLOY POWDERS

[76] Inventor: Pei Sung, 30 Buckspark Ct., Potomac, Md. 20854

[21] Appl. No.: 175,378

[22] Filed: Aug. 5, 1980

Related U.S. Application Data

[63] Continuation-in-part of Ser. No. 61,982, Jul. 30, 1979, abandoned.

[51] Int. Cl.$^3$ .............................................. C22C 30/00
[52] U.S. Cl. .................................... 75/255; 75/173 C
[58] Field of Search ............. 75/255, 134, 169, 173 C

[56] References Cited

U.S. PATENT DOCUMENTS 3,305,356  2/1967  Youdelis ............................... 75/134
3,980,472  9/1976  Asgar et al. ........................... 75/169
4,030,918  6/1977  Sung et al. ......................... 75/173 C

*Primary Examiner*—Upendra Roy

[57] ABSTRACT

A new low silver dental alloy powder combinations consists
(1) 75% to 95% by weight metal alloy particles with a composition of 45% to 60% silver, 26% to 33% tin and balanced with pure copper.
(2) 5% to 25% by weight silver-copper or silver-copper-indium alloy powders.

The said combination mixed with equal amounts of mercury, the corrosive phase ($\gamma_2$) has been eliminated.

2 Claims, No Drawings

γ2 - FREE, LOW COST AMALGAM ALLOY POWDERS

This application is a continuation-in-part of my application Ser. No. 061,982 filed July 30, 1979, application now abandoned.

The present invention relates to dental amalgam composition.

Amalgamatable dental alloy have been used for many years. These dental alloys at least the conventional ones, contained from 65 to 75% silver, 20 to 30% tin and up to 6% copper and 2% zinc. The conventional alloys, when amalgamated with mercury, form a substantial amount of γ2, gamma-2 phase which is corrosive and is detrimental to the final properties of restorations. In recent years, new amalgam compositions have been developed; basically, wherein the copper content is increased which in turn reduces the γ2 phase and improves the corrosion resistance of the amalgam.

Among the improvements, Youdelis (U.S. Pat. No. 3,305,356 February, 1967) describes a mechanical mixture of a silver base alloy to the conventional dental amalgam powders. The conventional dental amalgam powders contain essentially 75% by weight silver and 25% by weight of tin, said alloy having up to 7% of silver-tin alloy replaced by up to 5% by weight of copper and up to 2% by weight of zinc. The silver base alloy contains at least 50% by weight of silver. Asgar (U.S. Pat. No. 3,980,472 September, 1976) claims a metal powder for use in the preparation of dental restorations comprising of a mechanical mixture containing 55 to 90% of a silver base amalgamatable alloy and 10 to 45% of a nonamalgamatable powder, said first powder consisting at least 65% silver, up to 6% copper and 2% zinc and at least 25% tin, said second powder consisting of about 1 to 20% tin in balanced with silver, and a third alloy constituent individually selected from the group consisting of 5% to 50% zinc, 5 to 50% aluminum, copper in an amount to provide a silver to copper ratio of about 2.6:1, up to 30% indium in combination with copper. Sung (U.S. Pat. No. 4,030,918 June, 1977) describes a single component which is not a mechanical mixture, dental alloy powder comprising homogeneous particles having a composition of 35 to 50% silver, 20 to 30% copper, 25 to 35% tin and 2 to 8% indium. Weikel (U.S. Pat. No. 3,954,457) claims that a dental alloy powder consisting of (1) conventional silver base alloy with a composition of 65% silver, 29% tin, up to 6% copper and up to 2% zinc and (2) a silver copper alloy powders. Wolf (U.S. Pat. No. 3,841,860 Oct., 1976) describes the addition of silver-copper-tin alloy particles into a conventional alloy containing 68 to 72% by weight silver, 22 to 28% of tin and between 1 and 8% of copper.

The present invention is directed to an improvement over the above prior art. What I have discovered is an alloy mixture that is low cost, amalgamatable and easily handled, and has excellent initial and long term compressive strengths. The said alloy consists of (1) 75 to 95% by weight of alloy powders which contain a much lower percentage of silver (i.e. 45 to 60% silver, 26 to 33% tin and balanced with copper) in comparison to the conventional dental amalgam component, and hence, is economical, and (2) 5 to 25% silver-copper base alloy powders which contains 45% silver minimum with or without 2% indium in maximum. The following Tables describes the fundamental differences between the present invention and the related prior arts.

| COMPARISON TABLE BETWEEN THE PRESENT INVENTION AND THE PRIOR ARTS | | |
|---|---|---|
| PRESENT INVENTION | Youdelis (U.S. Pat. No. 3,305,356) | Asgar (U.S. Pat. No. 3,980,472) |
| Mixture of following components:<br>(1) Improved amalgam powders with 45 to 60% silver, 26 to 33% tin balanced with copper<br>(2) Silver-copper alloy powders with or without indium. (45% minimum silver with 0 to 2% indium maximum) | Mixture of following components:<br>(1) Conventional amalgam powders with 65% silver minimum, a typical composition is 69% silver, 25% tin, 4% copper and 2% zinc<br>(2) Nonamalgamable alloy powders with a composition of 50 to 72% silver in balanced with copper and others | Mixture of the following components:<br>(1) Conventional amalgam powders with 65% silver minimum, a typical composition is 69% silver, 25% tin, 4% copper and 2% zinc<br>(2) Nonamalgamable alloy powders with 1 to 20% tin in balanced with silver and others |

The improved amalgam powders of this invention can be obtained from the following techniques: (1) lathe cut from an ingot as described in example "1" of this application and (2) gas or water atomized powder from melts.

What I have discovered is a new dental alloy that is amalgamable with from 45 to 55% mecury. It is important in this new dental alloy to maintain the low percent of silver. If more silver is present, my new alloy will not have the proper setting time and the initial strength. It is also important that the indium should be kept as low as possible in 1% range. High percentage of indium will prolone the setting time of the amalgam. It is believed that the unexpected results of the present invention of low silver content, gamma-2 free composition are derived from the solid state reactions among silver, copper and tin to form $Cu_3Sn$, $Cu_6Sn_5$ and Ag-Hg phases.

The following examples demonstrate prefered alloy compositions in accordance with the present invention. It should be noted that all percentages are given in weight percent throughout this specification.

EXAMPLE 1

Two different melts, hereinafter called melt A and melt B are made. Melt A comprises 300 grams of silver, 145 grams of tin and 55 grams of pure copper. Melt B comprises 250 grams of silver, 150 grams of tin and 100 grams of pure copper. Both compositions are melted in an electric resistance furnance at 1200° C. The composition of the final melt A contains 59.6% silver, 28.9% tin and 11.5% copper. The final composition of Melt B contains 50.3% silver, 29.8% tin and 19.9% copper. The melts were cast in a 2 inch diameter graphite mold and cooled to room temperature. The cast ingots were annealed at 400° C. for overnight and allowed to cool to room temperature in air. The ingots were then mounted on a mechanical lathe at a rotating speed of 80 rpm. The 30° tooling steel is used to cut the ingot into powder form. The transversal speed of cutting tool is controlled at 0.00075 inches per revolution. The filings formed are ball milled and screened through a 325 mesh screen. The less than 325 mesh powder is then annealed at 200° C. for one hour. The physical properties of the resultant amalgam were measured according to American Dental specification #1 for dental amalgam. The $\gamma_2$-phase was determined by using X-Ray diffraction as indicated by Sung et. al, (U.S. Pat. No. 4,030,918 June, 1977). Table I shows the measured amalgam properties:

TABLE I

|  | MELT A | MELT B |
| --- | --- | --- |
| Mercury to Powder Ratio | 1:1 | 1:1 |
| $\gamma_2$-phase | present | present |
| set time (min) | 6½ to 7 | 4½ to 5 |
| one hour compression strength (psi) | 23,100 | 26,570 |
| 24 Hrs. compression strength (psi) | 56,420 | 59,730 |
| Creep (%) | 1.1 | 0.86 |

EXAMPLE II

The alloy powders obtained from example I, after mixed with 10% and 20%, −400 mesh silver-copper alloy powders which contain 72% silver and 28% copper were triturated with mercury. The amalgam properties were then measured as listed in Table II.

TABLE II

|  | MELT A | | MELT B | |
| --- | --- | --- | --- | --- |
| % of Ag—Cu powders by weight | 10% | 20% | 10% | 20% |
| mercury to powder ratio | 1:1 | 1:1 | 1:1 | 1:1 |
| $\gamma_2$-phase | present | disappear | disappear | disappear |
| set time (min) | 4½ to 5 | 3 to 3½ | 3 to 3½ | 2 to 2½ |
| one hour compression strength (psi) | 25,650 | 27,400 | 27,150 | 26,320 |
| 24 Hrs. compression strength (psi) | 62,240 | 63,750 | 65,240 | 66,120 |
| Creep (%) | 0.8 | 0.4 | 0.6 | 0.4 |

EXAMPLE III

The alloy powders obtained from example I, after mixed with 20% by weight, −400 mesh, silver-copper-indium powders which contain 71% silver, 28% copper and 1% indium were triturated with mercury. The result of amalgam properties are listed in Table III.

TABLE III

|  | MELT A | MELT B |
| --- | --- | --- |
| % of Ag—Cu—In powder by weight | 20% | 20% |
| Mercury to powder ratio | 1:1 | 1:1 |
| $\gamma_2$-phase | none | none |
| set time (min) | 3 to 3½ | 2 to 2½ |
| one hour compression strength (psi) | 26,720 | 26,340 |
| 24 Hrs. compression strength (psi) | 67,780 | 72,540 |
| Creep (%) | 0.4% | 0.4% |

EXAMPLE IV

The alloy powders obtained from example I, after mixed with 20%, −325 mesh silver-copper alloy powders which contain 48% silver and 52% copper were triturated with mercury. The amalgam properties were then measured as following:

|  | melt A | melt B |
| --- | --- | --- |
| mecury to powder ratio | 1:1 | 1:1 |
| $\gamma_2$-phase | none | none |
| setting time (min) | 2½ to 3 | 2 to 2½ |
| one hour compression strength (psi) | 24,100 | 22,050 |
| 24 hours compression strength (psi) | 61,000 | 58,000 |

The present invention has been described in terms of presently known preferred embodiments and it is intended the compositions which may depart from those presently preferred which demonstrate the novel advantages of use are to be included in the scope of the appended claims.

What is claimed is:

1. A dental alloy powder consisting of a mixture of 75% to 95% by weight of metal alloy powder which consists of 45% to 60% silver, 26% to 33% tin balance pure copper and 5% to 25% by weight of silver-copper alloy powder which consists of minimum 45% silver balance copper.

2. A dental alloy powder consisting of a mixture of 75% to 95% by weight metal alloy powder which consists of 45% to 60% silver, 26% to 33% tin balance pure copper and 5% to 25% by weight of silver-copper-indium alloy which consists of minimum 45% silver and maximum of 2% indium balance copper.

* * * * *